(12) United States Patent
Ostler et al.

(10) Patent No.: US 7,283,230 B2
(45) Date of Patent: Oct. 16, 2007

(54) SEMICONDUCTOR FORENSIC LIGHT KIT

(75) Inventors: Calvin D. Ostler, Riverton, UT (US); Densen Cao, Sandy, UT (US); Hongyan Li, Sandy, UT (US); Zhaohui Lin, Salt Lake City, UT (US)

(73) Assignee: CAO Group, Inc, West Jordan, UT (US)

( * ) Notice: Subject to any disclaimer, the term of this patent is extended or adjusted under 35 U.S.C. 154(b) by 432 days.

(21) Appl. No.: 11/112,731

(22) Filed: Apr. 22, 2005

(65) Prior Publication Data

US 2005/0231966 A1  Oct. 20, 2005

Related U.S. Application Data

(63) Continuation-in-part of application No. 10/360,327, filed on Feb. 7, 2003, now abandoned, and a continuation-in-part of application No. 10/361,090, filed on Feb. 7, 2003, now Pat. No. 6,954,270, and a continuation-in-part of application No. 10/189,224, filed on Jul. 3, 2002, now Pat. No. 6,979,194, and a continuation-in-part of application No. 10/016,992, filed on Dec. 13, 2001, now Pat. No. 7,094,054, which is a continuation-in-part of application No. 09/405,373, filed on Sep. 24, 1999, now Pat. No. 6,331,111.

(60) Provisional application No. 60/435,526, filed on Dec. 20, 2002, provisional application No. 60/304,324, filed on Jul. 10, 2001.

(51) Int. Cl.
*G01J 3/30* (2006.01)
*F21V 29/00* (2006.01)

(52) U.S. Cl. .................................... 356/317; 362/294

(58) Field of Classification Search ..................... None
See application file for complete search history.

(56) References Cited

U.S. PATENT DOCUMENTS

| | | | | |
|---|---|---|---|---|
| 5,072,338 A * | 12/1991 | Hug et al. | ................... | 362/553 |
| 5,515,162 A * | 5/1996 | Vezard et al. | ................ | 356/318 |
| 5,581,356 A * | 12/1996 | Vezard | ....................... | 356/418 |
| 5,613,752 A * | 3/1997 | Vezard | ....................... | 362/552 |
| 6,719,559 B2 * | 4/2004 | Cao | ............................ | 433/29 |
| 6,755,649 B2 * | 6/2004 | Cao | ............................ | 433/29 |
| 6,862,093 B2 * | 3/2005 | Peng et al. | ................. | 356/418 |
| 6,890,175 B2 * | 5/2005 | Fischer et al. | ................ | 433/29 |
| 7,098,469 B1 * | 8/2006 | Carrington | .............. | 250/504 H |
| 2005/0254237 A1 * | 11/2005 | Nath et al. | ................... | 362/190 |

* cited by examiner

*Primary Examiner*—Gregory J. Toatley, Jr.
*Assistant Examiner*—Jonathan Skovholt
(74) *Attorney, Agent, or Firm*—Geoffrey E. Dobbin

(57) ABSTRACT

A semiconductor forensic light kit is disclosed. The forensic light kit may use a variety of semiconductor light sources to produce light that contrasts forensic evidence against its background for viewing, photographing and collection. Example semiconductor light sources for the forensic light kit include light emitting diodes and laser chips. A heat sink, thermoelectric cooler and fan may be included to keep the forensic light cool. Removable light source heads may be included on the forensic light kit to provide for head swapping to give the user access to different wavelengths of light.

16 Claims, 6 Drawing Sheets

SEMICONDUCTOR FORENSIC LIGHT KIT

CROSS REFERENCE TO RELATED APPLICATIONS

Figure 1:
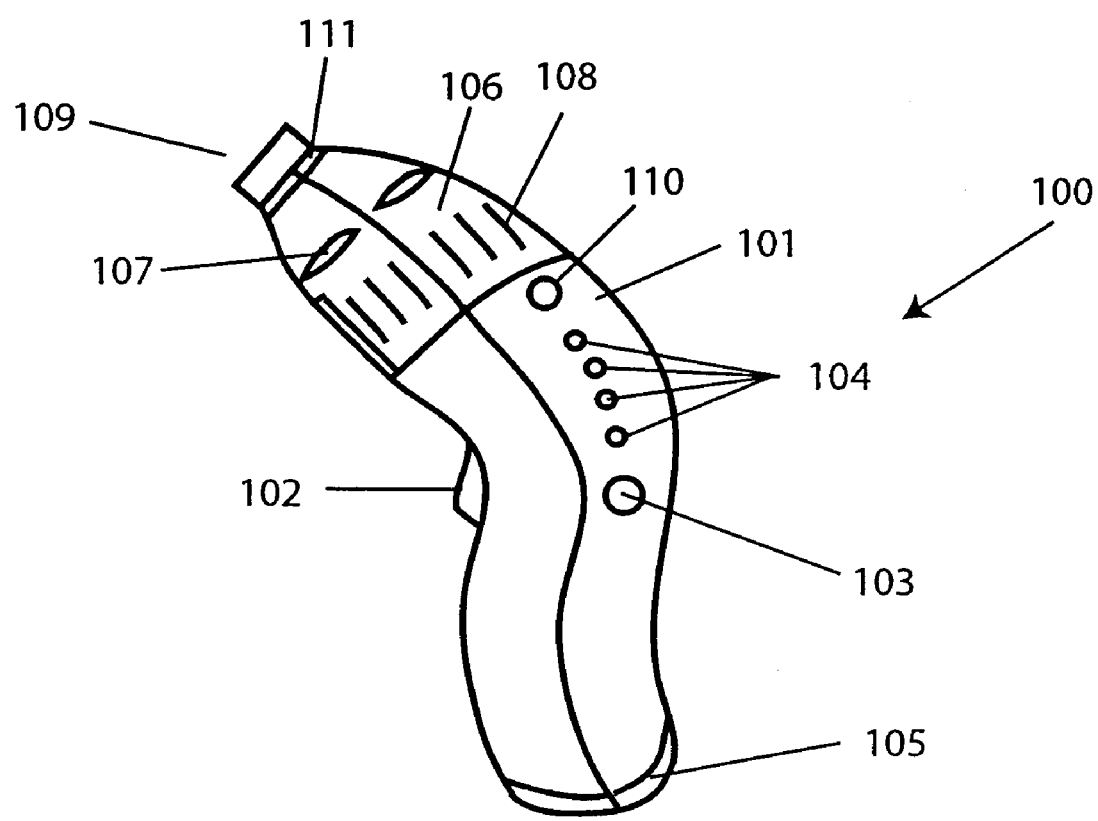

This patent application is a continuation-in-part to U.S. patent application Ser. No. 10/360,327 filed on Feb. 7, 2003, now abandoned, and a continuation-in-part to U.S. patent application Ser. No. 10/361,090 filed on Feb. 7, 2003, now U.S. Pat. No. 6,954,270, both of which claim priority to claimed to U.S. Provisional Patent Application Ser. No. 60/435,526 filed on Dec. 20, 2002, each of which is hereby incorporated by reference. This patent application is also a continuation-in-part to U.S. patent application Ser. No. 10/189,224 filed on Jul. 3, 2002, now U.S. Pat. No. 6,979,194, which claims priority to U.S. Provisional Patent Application Ser. No. 60/304,324 filed on Jul. 10, 2001, and which is also a continuation-in-part of U.S. patent application Ser. No. 10/016,992 filed on Dec. 13, 2001, now U.S. Pat. No. 7,094,054, which is a continuation-in-part of U.S. patent application Ser. No. 09/405,373 filed on Sep. 24, 1999, now U.S. Pat. No. 6,331,111, each of which is hereby incorporated by reference.

BACKGROUND

In the field of forensic science, there is a need for a way to detect various evidence that may be used in a criminal prosecution, including blood, saliva, other body fluids, hair, flesh, bone fragments, teeth, human skin damage such as bruises, bite marks or cuts, shoe prints, fingerprints, footprints, tire prints, gunpowder residue, bullets and portions thereof, explosive devices, explosive materials, parts of explosives, chemical weapons, chemical agents, biological weapons, paint, grease or oil, glass fragments, metal rubbings, fibers, dust patterns, various trace evidence, alteration of documents (forgery, different inks), narcotics, herbal evidence, and components, residues and traces thereof.

In the past, forensic personnel used high intensity conventional light sources, such as halogen bulbs, or ion gas laser light sources in order to illuminate areas of a crime scene and attempt to detect evidence since some evidence such as fingerprints do not fluorescence brightly alone. Contrast between such evidence being sought and the background against which it was found was sometimes achieved by using fluorescent dusting powder, dye, or other marker material, and light having a wavelength that substantially coincides with a known excitation wavelength of the marker. The characteristic of the marker is that, upon illumination with light at one of its excitation wavelengths, it will fluoresce, or emit light. Such fluorescence is typically at a longer wavelength as compared to the excitation wavelength. Examination of evidence was also enhanced through the use of color filtering glasses or barrier filters, whose color filtering characteristics are tuned to maximize the image to be detected. The forensic lights in the past had numerous drawbacks including bulky size, need for access to an AC power supply, and high cost.

SUMMARY

Various structures and components of a forensic light that uses a semiconductor light sources are disclosed.

DETAILED DESCRIPTION

Referring to FIG. 1, an example forensic light 100 is depicted. It includes a housing 101 that houses various components of the forensic light, such as control circuitry and the battery pack. On the top of the housing 101, there is a power level selection button 103 for selecting full power in different level, and display lights (such as LED indicator lights) for indicating power level of light operation. Different power level operations may be needed for different detection purposes. Optionally, a tripod mounting attachment mechanism for camera use may be included. On the bottom of the housing there is a trigger 102 for initiating and terminating light output from the forensic light. Since the forensic light produces light of an intensity that can damage the human eye, a spring loaded trigger may be provided so that if a user is not actively soliciting light output by squeezing the trigger, output of light from the forensic light will cease. A battery pack or a power pack 105 may be included at the proximal end of the housing or main light body. The light can be operated by battery if the battery pack is used and the light can be operated by AC power using a switching power supply or by use of an automobile DC adaptor when a power pack is used. A light head 106 may be provided at the distal end of the housing or main light body that may be removable from the housing 101 or main body of the forensic light. The light head 106 may contain the light source and other components. Since the light source produces heat as well as light, it may be desirable to include ventilation apertures 108 that permit air to enter the light head to provide a cooling effect. Additionally, air exit vents 107 are provided for air circulation through the light head. Light beams will exit the light head at the exit aperture 109 which may include a protective cover to prevent dirt or moisture from damaging the light source and which may also protect the light source from mechanical damage. In the light head, an adapter 111 may be included to permit viewing of forensic evidence through filters, focusing lenses, diffusers and polarizers.

Figure 2A:
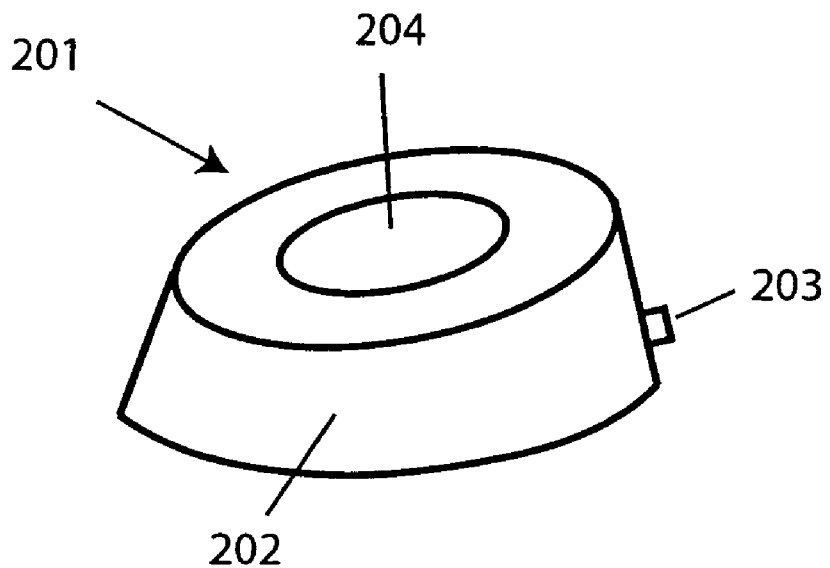

Referring to FIG. 2a, if it is desired to have a battery-operated forensic light, then a battery charger 201 may be provided. The battery charger may include a body 202 with a periphery on which a receptacle 203 may be provided for receiving electrical power. A battery receptacle 204 may be provided for receiving batteries or a power pack for charging. The battery used in the light operation is embedded in a battery pack. The battery charger can be operated by a AC power or an automobile DC adapter power supply.

Figure 2B:
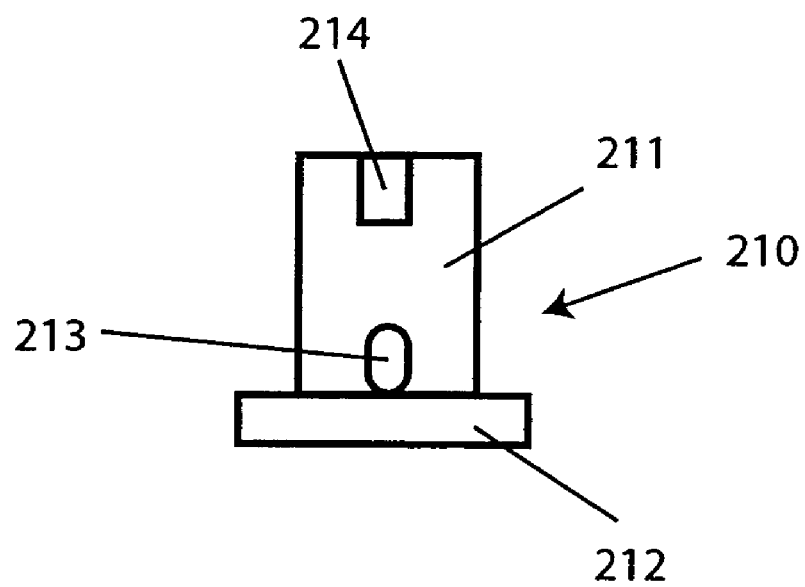

Referring to FIG. 2b, an example battery pack or power pack 210 is depicted. The battery pack 210 may include a plastic casing 205, a base 205, a lock 208 and an electrical contact 208.

Figure 3:
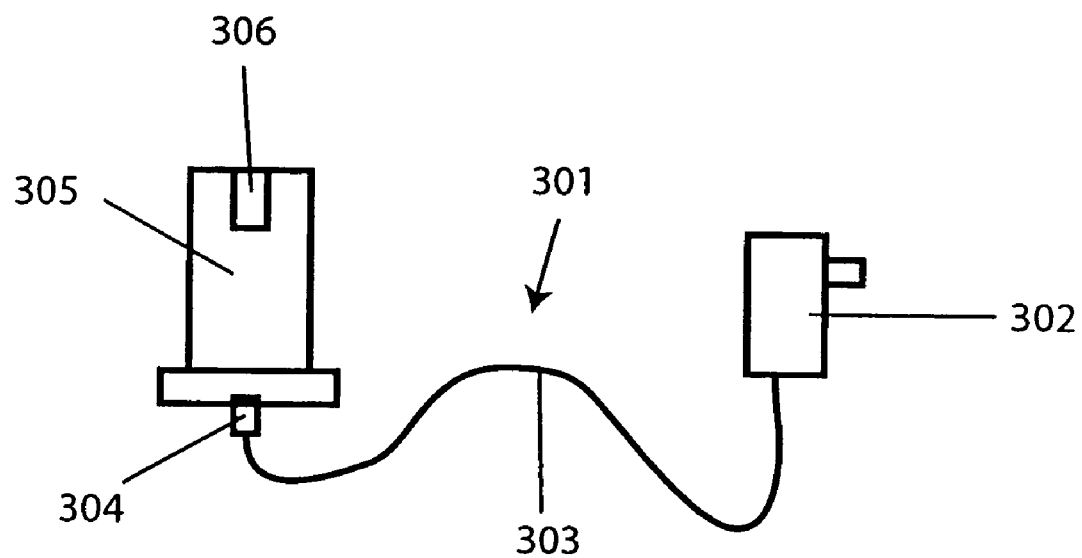

Referring to FIG. 3, a power pack unit 301 may be provided for operating the forensic light. The power pack 301 includes an AC power supply and plug 302 to receive AC power and convert it to DC power, a cable or wire 303 to conduct electrical power, and a plug 304 to connect the cable to the power pack 305. There is an electrical connection 306 for the power pack to contact electronic circuitry within the forensic light. The physical configuration of the power pack 305 is the same as battery pack so that the light unit can be operated by either battery pack or AC power using a power pack.

Figure 4:
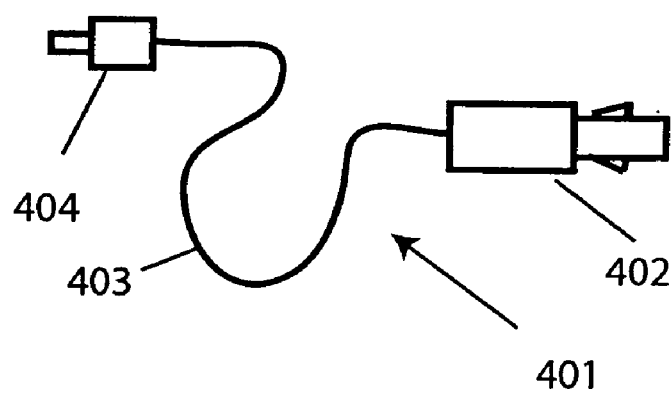

Referring to FIG. 4, a provision has been made to operate the forensic light by use of a DC adapter. This allows for convenient use of the forensic light in an automobile. The DC adaptor 401 has a DC plug 402 to fit into universal DC outlet such as found in an automobile, a cable or wire 403 to conduct power, and a plug 404 to connect the DC adapter to a power pack such as that depicted in FIG. 3.

By assembling a kit of the foregoing components, a forensic light kit may be provided that is powered by a battery pack, AC power or DC power, at the user's discretion. Such a kit may include other components such as the light heads of different wavelengths disclosed below and other desired hardware such as filters, glasses, etc.

Figure 5:
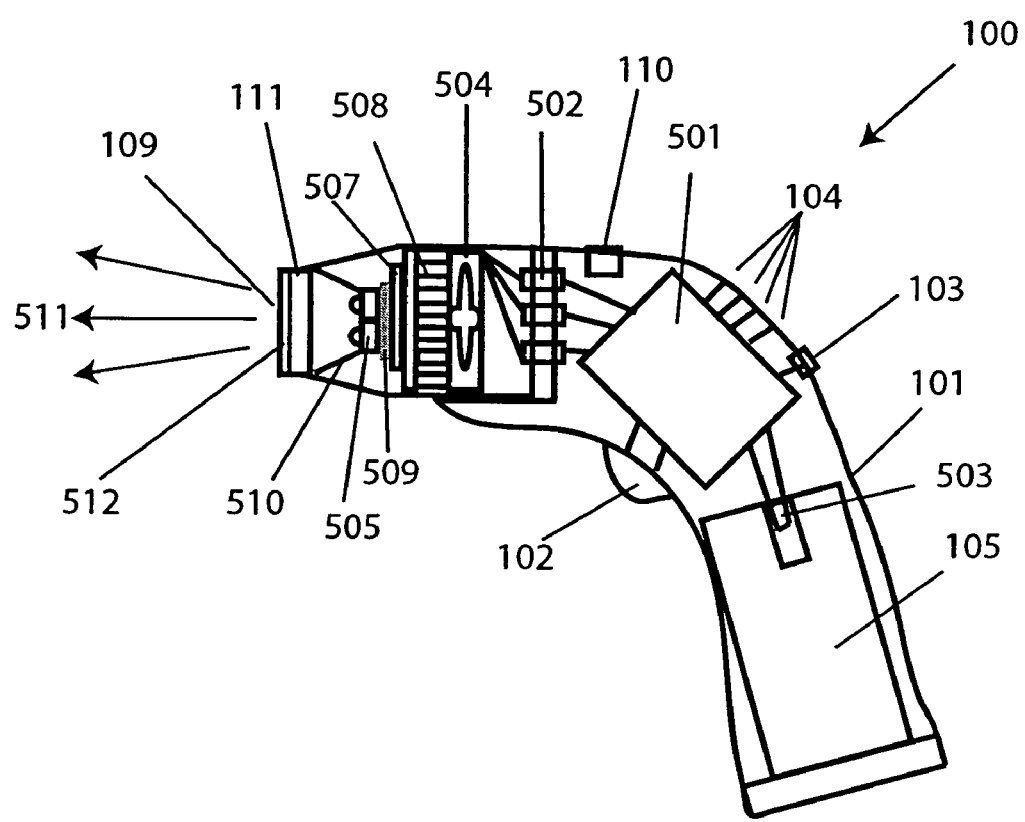

Referring to FIG. 5, a cross sectional view of the forensic light 100 of FIG. 1 is depicted. Control circuitry 501 is provided for controlling operation of the light. The control circuitry controls the on/off function of the forensic light as well as light intensity. Electrical connections 502 are provided for establishing electrical contact between the main light body and the removable light head. The control circuitry is also connected to the power supply (either battery pack or power pack as described above) through connection 503. A fan 504 may be provided within the light head for air circulation and heat dissipation. Individual semiconductor light producing devices 505 such as light emitting diode (LED) modules (including LED chip mounted on a primary heat sink and covered by a cover or plastic dome) or laser chips are mounted on the distal side of a thermoelectric ("TE") cooler 507 which is affixed to a secondary heat sink 508 that dissipates most of the heat produced by the light producing devices. The semiconductor light producing devices may be mounted to a heat sink by heat conductive adhesive 509. The TE cooler is optional and may be used in some applications. The proximal side of the secondary heat sink 508 has a finned or comb-shaped wings to increase the surface area of the secondary heat sink in order to increase contact of the heat sink with air and improve heat dissipation. Air from the fan moves past the secondary heat sink for heat dissipation. A light reflector 510 such as a conical or parabolic reflector may be provided to collect light from the semiconductor light producing devices and direct it through a light exit aperture 109 and/or cover or focus lens to produce useful light beams 511. An optional protective cover or focus lens 512 may be included at the light exit to protect electronic components from dirt and physical damage. If a focus lens is used, it can be used to concentrate the light beam and determine a desired light footprint. The number of semiconductor light producing devices can vary from 1 to any desired number based on the power levels desired in the forensic light.

Figure 6:
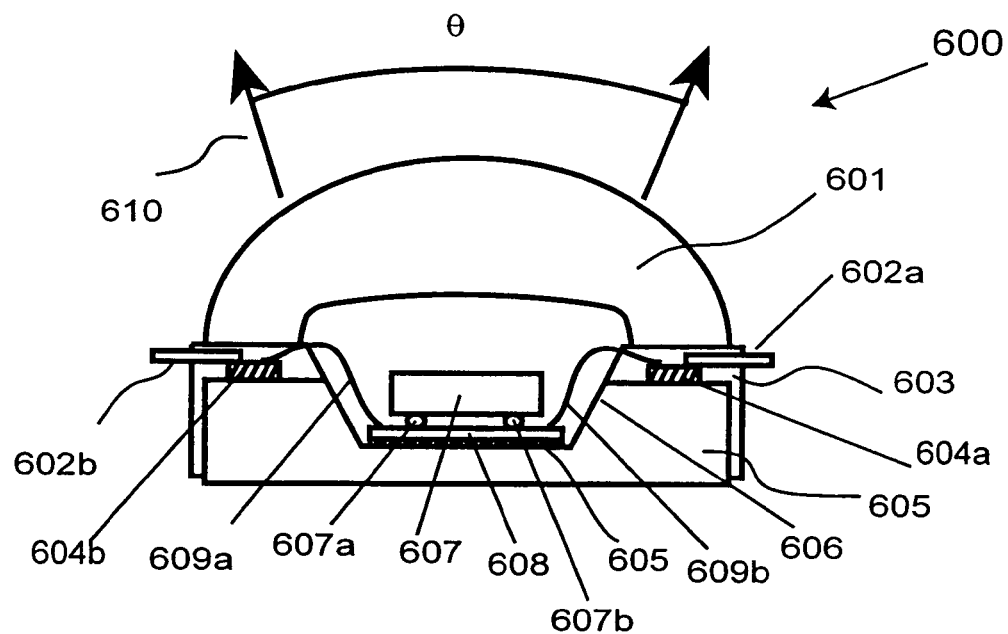

FIG. 6 depicts a side view of an LED module 600 according to a flip-chip design that can serve as a light source for a forensic light. The light source 600 includes a cover or dome 601 that serves to protect the LED(s) within from contamination from moisture and dirt and from mechanical damage. The dome 601 may also serve to focus light emitted by the LED. A light emitting diode chip array 607 is mounted in inverted position in a well 606 of a heat sink 605 according to the so-called 'flip chip' design. In this example, the chip has an insulative substrate. The chip 607 is mounted on a flip chip pad 608 within the well 606. Electrode beads or bumps 607a and 607b separate the chip from the pad but attach the chip to the pad and provide electrical connection. The pad is affixed to the bottom of the well by a method such as soldering, brazing, welding or use of a heat-conductive adhesive 605. The chip has an electrode on top and its epitaxial layers (semiconductor material) facing down toward the pad and the bottom of the well in the figure. The pad upper surface may be light reflective so that light is reflected from the pad in a useful direction. The pad may be coated with a light reflective film, such as Au, Al or Ag. The heat sink may be surrounded by an insulative jacket 603. The chip is powered via wires 609a and 609b attached to intermediate islands 604a and 604b which are in turn contacted by wires 602a and 602b. Light from the light source is emitted as a beam 610 having an angle of departure θ that is defined and determined in part by the angle of the walls of the well as well as by any focusing or restrictive characteristics of the dome. In such a package, all of the light emitted from the chip can be reflected back in the light exit direction for highest light output. The well may also include a reflective coating or polished surface.

Figure 7:
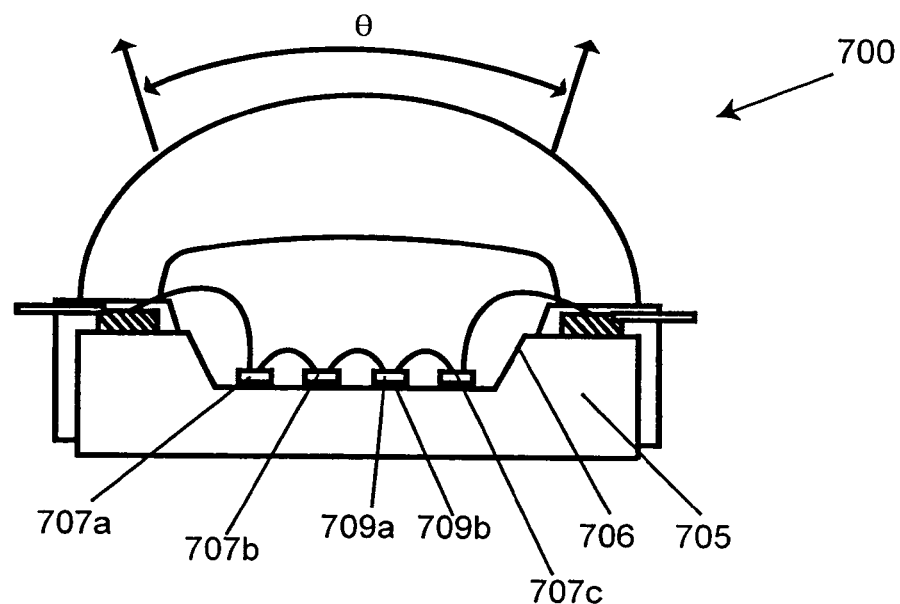

FIG. 7 depicts an LED module 700 that includes a well 706 within a heat sink 705 and having a plurality or array of LED chips 707a, 707b, 707c, etc. within the well. The depth of the well can be from 0 mm to more than 50 mm. Each individual LED chip may include semiconductor material or epitaxial layers 709a on a substrate 709b. Each chip may be mounted to the heat sink by use of heat conductive adhesive or other mounting means. The chips in this figure are wired in series, although wiring in parallel is also possible when the application requires it. The remainder of the features of the LED 700 module are similar to those already discussed.

Figure 8:
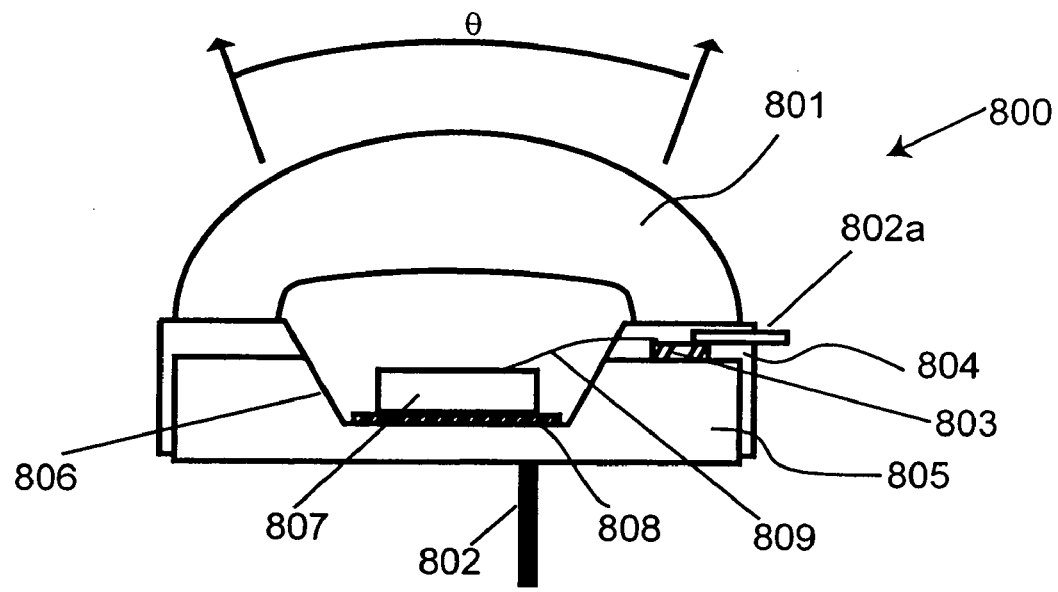

FIG. 8 depicts a semiconductor light emitting module 800 that has a single LED or laser chip 807 mounted in a well 806 of a heat sink 805. The chip 807 has a conductive substrate and may be mounted to the floor of the well of the heat sink by use of a heat conductive adhesive. The depth of the well can be from 0 mm to more than 50 mm. The chip is powered by wire 809 from island 803. A wire lead 802a brings electrical power to the module. An insulative jacket 804 may be placed around the heat sink for electrical insulation. A negative electrode 802 is provided on the bottom of the heat sink for electrical conduction.

Figure 9:
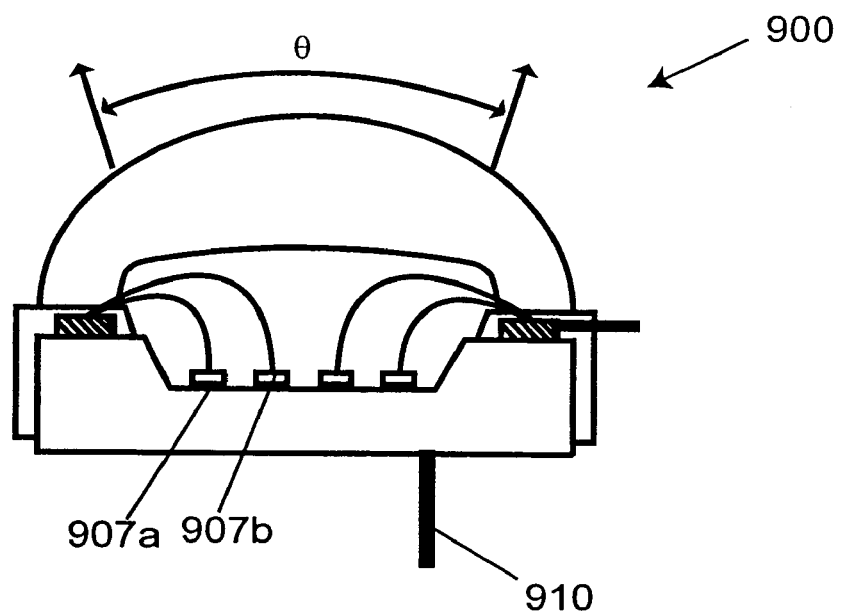

FIG. 9 depicts an LED module 900 that includes an array of semiconductor light producing chips 907a, 907b, etc. within a well of a heat sink. The chips use an electrically conductive substrate and there is a negative electrode 901 on the heat sink for electrical connection.

For forensic light sources with multiple semiconductor light producing chips, the quantity of chips used may vary depending on application, and can range from 1 to several hundred. The spacing between chips can be adjusted from zero to more than 1 mm, depending on the application requirements. The semiconductor chip producing light may be a single chip or single chip array. The chip or chips may be mounted in a well of a heat sink or may be mounted directly on a heat sink. The wavelength of light emitted from each chip in a multi-chip forensic light design may be the same wavelength or different wavelengths to cover a desired light spectral range. If a well is provided in the heat sink, the depth of the well may be as desired, such as from 0 to 50 mm or more, depending on application.

The forensic light source may be constructed with the chip(s) mounted to the primary heat sink, such as by use of a heat conductive and/or light reflective adhesive. The primary heat sink can be attached to a secondary heat sink if desired, such as by use of a heat conductive and/or electrically insulative adhesive, welding, brazing, soldering or mechanical fixation.

The chip(s) may be any of those described herein or otherwise, such as a flip chip design. The primary heat sink, chip(s) and dome can be combined as a light module. A cover may be provided over the dome. An example cover would include a plastic fitting or attachment and a glass window through which light may travel. Glass generally has better light transmission qualities than plastic, but either could be used. The dome can serve as a focusing lens.

A reflective cone may be included in the forensic light, such as between the dome and the light exit or apeture from which light exits the forensic light. The cone can be used for a light conservation purpose, to capture and use light that would be errant and would otherwise be wasted. The cone can also be used for the purpose of beam shaping and to create a light beam with a desired footprint. Example light beam footprints include circular, oval, square, rectangular, and any other geometric shape, depending on application. The footprint can be any desired size for the application. A shaped beam can have superior light intensity. The reflective cone can have an interior surface that reflects light. Some cones may reflect at least as much as 85% of the light that encounters them. Materials of cones can be plastic or metal, polished or plated metal such as aluminum or alloy, or otherwise. Use of a cone allows superior maintenance of light beam intensity as distance from the chip(s) increases.

Heat sinks are often a combination of two different kinds of materials, the first with a low thermal expansion rate and the second with high thermal conductivity. Monolithic heat sinks may be used as well. Examples of some heat sink materials which may be used in lights depicted herein include metals, copper, aluminum, silver, magnesium, steel, silicon carbide, boron nitride, tungsten, molybdenum, cobalt, chrome, Si, $SiO_2$, SiC, AlSi, AlSiC, natural diamond, monocrystalline diamond, polycrystalline diamond, polycrystalline diamond compacts, diamond deposited through chemical vapor deposition and diamond deposited through physical vapor deposition, and composite materials or compounds. Any materials with adequate heat conductance and/or dissipation properties can be used. If desired, a heat sink may have fins or other surface modifications or structures to increase surface area or promote air flow and enhance heat dissipation.

Examples of heat conductive and/or electrically insulative adhesives that may be used are silver based epoxy, other epoxies, and other adhesives with a heat conductive quality and/or electrically insulative quality. In order to perform a heat conductive function, it is important that the adhesive possess the following characteristics: (i) strong bonding between the materials being bonded, (ii) adequate heat conductance, (iii) electrically insulative or electrically conductive if desired (or both), and (iv) light reflectivity if desired, or any combination of the above. Examples of light reflective adhesives which may be used to affix chips to a heat sink include silver and aluminum based epoxy. One example heat conductive and electrically insulative adhesive includes a mixture of a primer and an activator. In this example, the primer may contain one or more heat conductive agents such as aluminum oxide (about 20-60%) and/or aluminum hydroxide (about 15-50%). The primer may also contain one or more bonding agents such as polyurethane methacrylate (about 8-15%), and/or hydroxyalkyl methacrylate (about 8-15%). An activator may be mixed with the primer to form an adhesive. The activator may include any desired catalyst, for example n-heptane (about 5-50%), aldheyde-aniline condensate (about 30-35%), isopropyl alcohol (about 15-20%), and an organocopper compound (about 0.01 to 0.1%). Adhesives such as described herein can be used to mount a chip to a primary heat sink, or to mount a primary heat sink to a secondary heat sink, or both.

Examples of substrates on which the semiconductors used in the forensic lights depicted herein may be grown include Si, GaAs, GaN, ZnS, ZnSe, InP, $Al_2O_3$, SiC, GaSb, InAs and others. Both electrically insulative and electrically conductive substrates may be used.

Epitaxial layers and structures of semiconductor light emitting chips useful in forensic lights disclosed herein may include a substrate (such as sapphire) that serves as a carrier pad or platform on which to grow the chip's epitaxial layers. The first layer placed on the substrate may be a buffer layer (such as a GaN buffer layer). Use of a buffer layer reduces defects in the chip that would otherwise arise due to differences in material properties between the epitaxial layers and the substrate. Then a contact layer, such as n-GaN, may be provided. A cladding layer such as n-AlGaN Sub may be present to confine injected electrons. An active layer may be provided to emit the light when excited by electrons. An example active layer is such as InGaN with multiple quantum wells. The active layer is where electrons jump from a conduction band to valance and emit energy which converts to light. On the active layer, another cladding layer may be provided, such as p-AlGaN, to serve to confine electrons. A contact layer such as p+ GaN may be provided that is doped for Ohmic contact. The contact layer may have an electrode mounted on it.

The physical dimension of the chip(s), including their surface area, used in the forensic light can impact the intensity of the light produced. The chips could be of any desired size and shape, and might range from a surface area of more than about 300 um. Each individual chip may have a power output more than about 20 mW. The chips may emit light of any desired wavelength, including light from wavelengths ranging from 200 to 1500 nm.

Some examples of semiconductor light sources which may be desired to be used in a forensic light include light emitting diode chips, LED chip arrays (an LED chip with a large surface area and having paths of electrically conductive material projecting across some portions of its surface to power the chip), laser diodes, vertical cavity surface emitting laser, edge emitting lasers, surface emitting lasers, and others.

Example material which may be used in the TE cooler include include $Bi_2Te_3$, PbTe, SiGe, $BeO_2$, BiTeSe, BiTeSb, $AlO_3$, AlN, BaN and others.

Heat sinks used in the lights can be of a variety of shapes and dimensions, such as those depicted in the drawings or any others which are useful for the structure of the particular light source being constructed. It should be noted that the heat sink arrangement should be sufficient to prevent overheating of the semiconductor light source, or diminished light production and shortened product life may result.

A user of the forensic light will find it advantageous to select a light output frequency centered around a wavelength that tends to contrast the evidence being searched for against its background material. A table is provided below suggesting some wavelengths that may be desired for detecting various substances. Quick detachable light sources or heads for the forensic light may be manufactured that produce each of these specific wavelengths so that the forensic light user has a kit available with an array of different light sources available.

Correlation of Light Wavelength to Substance Searched for

| Color | Substance |
|---|---|
| UV (<400 nm) | Fingerprints |
| Near UV (405 nm) | human skin damage such as bruises, bite marks or cuts |

-continued

| Color | Substance |
|---|---|
| Blue (450 nm) | blood, saliva, other body fluids, hair, flesh, bone fragments |
| Green (525 nm) | shoe prints, fingerprints, footprints, tire prints, paint, grease or oil, glass fragments, metal rubbings, fibers, dust patterns, various trace evidence |
| Yellow (590 nm) | gunpowder residue, bullets, explosive materials |
| Red (630 nm) | alteration of documents (forgery), narcotics, herbal evidence |
| Infrared (>800 nm) | Document examination |

As desired, the forensic light may be configured to produce light that centers around a single wavelength, or multiple removable light sources capable of producing light of different wavelengths may be produced so that the user may select a light source of the appropriate wavelength for his application. In addition, if desired the forensic the light may be structured so that the user may select a light output power level that is less than full power output. For example, the forensic light may be structured so that the user may select a light output power level of ¼, ½, ¾ or full light output power. An example of light power output in milliwatts (mW) at those example levels for light centered on five (5) different wavelengths is shown in the table below.

Light Output Specifications (mW)

| Color | ¼ power | ½ power | ¾ power | Full power |
|---|---|---|---|---|
| UV (405 nm) | 100 | 200 | 300 | 400 |
| Blue (450 nm) | 250 | 500 | 750 | 1000 |
| Green (525 nm) | 200 | 400 | 600 | 800 |
| Yellow (590 nm) | 100 | 200 | 300 | 400 |
| Red (630 nm) | 100 | 200 | 300 | 400 |

It is possible for the forensic light to output light at any of a variety of different wavelengths, including but not limited to 280 nm, 350 nm, 400 nm, 405 nm, 450 nm, 525 nm, 590 nm, 630 nm, 800 nm, 980 nm, 1064 nm, 1300 nm and 1500 nm. Power output levels could be from less than 1 mW to more than 9000 mW.

The advantage of being able to produce light at less than the full light output power level is to provide contract against evidence background in different environment. It is also possible to produce forensic lights that have a fixed intensity power output. The forensic light may be used to fluoresce or illuminate evidence, to contrast it with a background, to fluoresce or illuminate the background to contrast it with evidence, or to otherwise use light in detecting the presence of evidence.

Some other advantageous features that the forensic light may include are discussed here. Portability is one such feature. The forensic light may be configured as a hand-held, battery-operated device that may be used at remote locations and may be easily transported and easily stored. The forensic light may be adaptable to other equipment such as a camera or image intensifying devices. The forensic light may be configured as a ring light that attaches to the font end of a camera lens and or image intensifying device thereby providing even illuminations of the desired field. In such a configuration the ring light could be constructed to accept filters, allowing the device to be removed from the equipment and used to view evidence directly in the same manner that a handheld magnifying glass would be used. Additionally, the forensic light may be configured to accept filters that positioned at the light output point intended to manipulate the output. Such filters could be a diffuser to soften or defocus the light being emitted, a focus lens to narrow the light beam intensifying the light over a small area, narrow-band pass for narrowing the wavelength band being emitted, and or polarizing filter to plane polarize the light being emitted. Such filters and lenses are readily and commercially available in a variety of sizes and shapes from several sources. Such a configuration would also allow the attachment of viewing filters and lenses for the user. The forensic light could be configured to accept both light output filters and lenses and viewing filters and lenses simultaneously. Another optional feature is a camera mount that allows the forensic light to be positioned with respect to a camera in order to photograph forensic evidence. Forensic lights may also used to provide light in the non-visible spectra (such as the UV and IR ranges) that reflects off the evidence and may be detected by a photon multiplier that in turn projects the light and image onto a view screen.

A forensic light constructed according to principles disclosed herein may be used to carry out a method for locating or detecting forensic evidence. Such a method may be designed or intended to locate various types of forensic evidence or materials that may later be used in a criminal prosecution, civil proceedings, or for other purposes. Examples of forensic evidence that a user of the forensic light may desire to gather include but are not limited to blood, saliva, other body fluids, hair, flesh, bone fragments, teeth, human skin damage such as bruises, bite marks or cuts, shoe prints, fingerprints, footprints, tire prints, gunpowder residue, bullets and portions thereof, explosive devices, explosive materials, parts of explosives, chemical weapons, chemical agents, biological weapons, paint, grease or oil, glass fragments, metal rubbings, fibers, dust patterns, various trace evidence, alteration of documents (forgery, different inks), narcotics, herbal evidence, and components, residues and traces thereof.

The method can include the steps of:
determining a type or class of forensic evidence sought to be discovered,
determining or selecting the wavelength of light that may be useful in detecting such forensic evidence, such as by contrasting such forensic evidence against its background,
obtaining, setting, building or modifying a semiconductor forensic light that outputs light of such wavelength,
illuminating a physical area with the light output by the forensic light in order to detect desired forensic evidence,
viewing any detected forensic evidence (viewing may take place through a filter, image intensifier if desired),
photograph the detected forensic evidence,
enhance or project any image of the evidence,
collect the detected forensic evidence, and
store the collected forensic evidence.

These method steps may be modified, steps may be omitted, or other steps may be added.

While the present lights have been described and illustrated in conjunction with a number of specific configurations, those skilled in the art will appreciate that variations and modifications may be made without departing from the principles herein illustrated, described, and claimed. The present invention, as defined by the appended claims, may be embodied in other specific forms without departing from its spirit or essential characteristics. The configurations of lights described herein are to be considered in all respects as only illustrative, and not restrictive. All changes that come within the meaning and range of equivalency of the claims are to be embraced within their scope.

The invention claimed is:

1. A semiconductor forensic light kit comprising:
   a battery charger, said battery charger being capable of charging a battery pack,
   an AC wall outlet cord for providing power to said battery charger,
   a DC power adapter and cord,
   a semiconductor forensic light that includes
   a housing having a proximal end, a distal end, a top, a bottom and an interior,
   control circuitry located in said housing interior,
   said control circuitry being able to control on/off and power intensity selection functions of the forensic light,
   an on/off button located on the top of said housing, said on/off button being in operable connection with said control circuitry,
   a power level selection button located on the top of said housing, said power level selection button accommodating the increase and decrease of light output levels from the forensic light,
   said power level selection button being in operable communication with said control circuitry,
   a trigger said housing, said trigger serving to accommodate initiation and terminate of light emission from the forensic light,
   said trigger being in operable communication with said control circuitry,
   a power pack located at said housing proximal end for providing electrical power to the forensic light,
   a plurality of light heads located at said housing distal end, each of said light heads emitting light centered on a different wavelength than each of said other heads,
   a light source within one of said light heads,
   said light source including
      a semiconductor light emitting device that can emit light of a wavelength useful in detecting forensic evidence,
      a primary heat sink to which said semiconductor light emitting device is affixed, said primary heat sink serving to draw heat away from said semiconductor light emitting device,
      a secondary heat sink to which said primary heat sink is affixed, said secondary heat sink serving to dissipate heat produced by said semiconductor light emitting device,
      a thermoelectric cooler located on said secondary heat sink, said thermoelectric cooler experiencing a drop in temperature when subjected to a voltage, and
      a fan serving to move air past said thermoelectric cooler in order to cool the light source,
   at least one ventilation aperture on said light head for permitting air to enter and exit the light head to facilitating heat dissipation, and
   at least one light exit on said light head, said light exit being sized and shaped to permit light to exit said light head for use in detecting forensic evidence.

2. A forensic light kit as recited in claim 1 wherein said light heads are detachable from said housing distal end.

3. A forensic light kit as recited in claim 1 wherein at least one of said light heads emits light of a wavelength centered about 450 nm.

4. A forensic light kit as recited in claim 1 wherein said semiconductor light producing device is an LED module that include the primary heat sink, an LED chip located in a well on the primary heat sink, and a dome over said LED chip, the LED chip including a substrate and epitaxial layers.

5. A forensic light kit as recited in claim 1 further comprising:
   a well in said primary heat sink, and
   a plurality of semiconductor light producing devices located in said well.

6. A forensic light kit as recited in claim 1 wherein at least one of said heat sinks includes a material selected from the group consisting of copper, aluminum, silver, magnesium, steel, silicon carbide, boron nitride, tungsten, molybdenum, cobalt, chrome, Si, $SiO_2$, SiC, AlSi, AlSiC, and diamond.

7. A forensic light kit as recited in claim 1 wherein said semiconductor light producing device includes epitaxial layers located on a substrate and wherein said substrate is selected from the group consisting of Si, GaAs, GaN, ZnS, ZnSe, InP, $Al_2O_3$, SiC, GaSb, and InAs.

8. A forensic light kit as recited in claim 1 wherein said semiconductor light producing device includes epitaxial layers located on a substrate, and at least one of the epitaxial layers is selected from the group consisting of:
   a buffer layer to reduce defects in the chip that may arise due to differences in material properties between the epitaxial layers and the substrate,
   a contact layer,
   a cladding layer serving to confine injected electrons, and
   an active layer that emits the light when excited by electrons, the light emitted being useful in forensic detection of evidence.

9. A forensic light kit as recited in claim 1 wherein said thermoelectric cooler includes a material selected from the group consisting of $Bi_2Te_3$, PbTe, SiGe, $BeO_2$, BiTeSe, BiTeSb, $AlO_3$, AlN, and BaN.

10. A forensic light kit as recited in claim 1 wherein said light head is capable of emitting light that is selected from the group consisting of blue, green, yellow, red, infrared and ultraviolet.

11. A forensic light kit as recited in claim 1 wherein light emitted by the forensic light is useful in detecting forensic evidence selected from the group consisting of blood, saliva, other body fluids, hair, flesh, bone fragments, teeth, human skin damage such as bruises, bite marks, cuts, shoe prints, fingerprints, footprints, tire prints, gunpowder residue, bullets and portions thereof, paint, grease, oil, glass fragments, metal rubbings, fibers, dust patterns, alteration of documents, narcotics, and herbal evidence.

12. A semiconductor forensic light kit comprising:
   a battery charger,
   a battery charger cord,
   a semiconductor forensic light that includes
   a housing having a proximal end, a distal end, a top, a bottom and an interior,
   a plurality of light heads located at said housing distal end, each of said light heads emitting light centered on a different wavelength than each of said other heads,
   each of said light heads being installable at said housing distal end,
   said light heads being quick detachable from said housing in order to accommodate removal of one light head and replacement of one of the light heads with another light head by a forensic technician working in the field,
   a light source within said light head, said light source including
- a semiconductor light emitting device that emits light of a wavelength useful in detecting forensic evidence,
- a primary heat sink to which said semiconductor light emitting device is affixed, said primary heat sink serving to draw heat away from said semiconductor light emitting device, and at least one light exit on said light head, said light exit being sized and shaped to permit light to exit said light head for use in detecting forensic evidence.

13. A forensic light kit as recited in claim 12 wherein said semiconductor light producing device is an LED module that include the primary heat sink, an LED chip located in a well on the primary heat sink, and a dome over said LED chip, the LED chip including a substrate and epitaxial layers.

14. A forensic light kit as recited in claim 12 wherein said heat sink includes a material selected from the group consisting of copper, aluminum, silver, magnesium, steel, silicon carbide, boron nitride, tungsten, molybdenum, cobalt, chrome, Si, $SiO_2$, SiC, AlSi, AlSiC, and diamond.

15. A forensic light kit as recited in claim 12 wherein said semiconductor light producing device includes epitaxial layers located on a substrate and wherein said substrate is selected from the group consisting of Si, GaAs, GaN, ZnS, ZnSe, InP, $Al_2O_3$, SiC, GaSb, and InAs.

16. A semiconductor forensic light kit comprising:

a power cord, a forensic light that includes a handle, a plurality of light heads locatable at said housing distal end, at least one of said light heads emitting light centered on a different wavelength than at least one of said other heads, at least one of said light heads being attachable to and removable from said housing, a light source within said light head, said light source including
- a semiconductor light emitting device that emits light of a wavelength useful in detecting forensic evidence,
- a primary heat sink to which said semiconductor light emitting device is affixed, said primary heat sink serving to draw heat away from said semiconductor light emitting device, and at least one light exit on said light head, said light exit being sized and shaped to permit light to exit said light head for use in detecting forensic evidence.

* * * * *